United States Patent [19]
Abboudi et al.

[11] Patent Number: 5,861,291
[45] Date of Patent: Jan. 19, 1999

[54] METHOD FOR PRODUCING PANCREATIN WHICH CONTAINS LOW AMOUNTS OF RESIDUAL ORGANIC SOLVENT AND PRODUCT THEREOF

[75] Inventors: Mouhsine El Abboudi, Sainte-Foy; Martin Beaulieu, Charny; Francis Bellavance, Saint-Romuald, all of Canada

[73] Assignee: Biozymes Inc., Quebec, Canada

[21] Appl. No.: 804,582

[22] Filed: Feb. 24, 1997

[51] Int. Cl.$^6$ .......................................................... C12J 9/94
[52] U.S. Cl. ......................... 435/186; 435/195; 435/198; 435/201; 435/219; 435/183
[58] Field of Search ..................................... 435/183, 195, 435/198, 201, 219, 186

[56] References Cited

U.S. PATENT DOCUMENTS

| | | |
|---|---|---|
| 3,168,448 | 2/1965 | Melcer et al. . |
| 3,223,594 | 12/1965 | Hock et al. . |
| 3,260,654 | 7/1966 | Toccaceli . |
| 3,844,891 | 10/1974 | Hess et al. . |
| 3,956,483 | 5/1976 | Lewis . |
| 4,019,958 | 4/1977 | Hell et al. . |
| 4,029,641 | 6/1977 | Hafner et al. . |
| 4,235,970 | 11/1980 | Leach et al. ............................ 435/202 |
| 4,280,971 | 7/1981 | Wischniewski et al. . |
| 4,623,624 | 11/1986 | Schultze . |

FOREIGN PATENT DOCUMENTS

| | | |
|---|---|---|
| 2634620 A1 | 2/1978 | Germany . |
| 4203315 A1 | 8/1992 | Germany . |
| WO 91/07948 | 6/1991 | WIPO . |

OTHER PUBLICATIONS

International Search Report International Application No. PCT/CA98/00135.
The United States Pharmacopeia—The National Formulary, 1990, United States Pharmacopeial Convention, Inc., USP XXII:1007–1011.

*Primary Examiner*—Leon B. Lankford, Jr.
*Attorney, Agent, or Firm*—Myers Bigel Sibley & Sajovec

[57] ABSTRACT

The present invention relates to an advantageous and novel method of producing pancreatin which contains low amounts of residual organic solvent, and more particularly to a method which is more environmentally friendly than conventional methods of pancreatin production. More specifically, the present invention relates to a method which utilizes quantities of organic solvents which are about 10 times lower than that of conventional methods. A preferred method of pancreatin preparation, whereby a pancreatic past is autolysed, decontaminated, subjected to an ultrafiltration, dried and then defatted is herein disclosed. The present invention further relates to a pancreatin preparation which contains low amounts of residual solvent. This amount is about 15 to 30 times lower than pancreatin preparation obtained with these conventional methods.

17 Claims, No Drawings

METHOD FOR PRODUCING PANCREATIN WHICH CONTAINS LOW AMOUNTS OF RESIDUAL ORGANIC SOLVENT AND PRODUCT THEREOF

FIELD OF THE INVENTION

The present invention relates to an advantageous and novel method of preparing pancreatin which contains low amounts of residual organic solvent, and more particularly to a method which is more environmentally friendly than conventional methods of pancreatin production. More specifically, the present invention relates to a method which utilizes quantities of organic solvents which are about 10 times lower than that of conventional methods. The present invention further relates to a pancreatin preparation which contains low amounts of residual solvent. This amount is about 15 to 30 times lower than pancreatin preparation obtained with these conventional methods.

BACKGROUND OF THE INVENTION

Pancreatin is a mixture of enzymes obtained by extraction of the pancreas which consists essentially of lipase, amylase and protease. A more detailed definition of pancreatin can be found for example in the United States Pharmacopeia-The National Formulary 1990 (United States Pharmacopeial Convention, Inc., USP XXII, starting at page 1007). Pancreatin has a variety of uses including uses in human and veterinary medicine, wherein it can be used to correct digestive deficiencies.

Pancreatin which consists of dried defatted pancreas is prepared from fresh or frozen pancreas by methods which are aimed at preserving the enzymatic activities present in the pancreas. Although pancreas from different animal origin can be used as the starting material, porcine pancreas is usually preferred due to its higher amylolytic and lipolytic activities.

The numerous known methods for producing pancreatin usually involve a treatment of the pancreas through an autolysis, a degreasing and a drying step (Lewis, U.S. Pat. No. 3,956,483). The autolysis step is determinant in producing a pancreatin having high enzymatic activities, since enzymes present in the pancreas need to be converted from their inactive form to their activated form. For example, the pro-enzymes of the proteases present in a comminuted, frozen or thawed pancreas are activated by the addition of trypsin and enterokinase and incubation thereof in the presence of water, salt solutions, or solvents such as glycerin, 25% ethanol and 20% acetic acid (U.S. Pat. No. 4,019,958, Hell et al.). Precipitation with inorganic salts, organic solvents, or tannins followed by a drying step are most generally performed on such extracts.

One particular method of autolysing a pancreas preparation is that of Schultze (U.S. Pat. No. 4,623,624) which teaches the use of isopropanol or acetone therefor and the obtention of a pancreatin preparation having a low germ count due to the isopropanol treatment. Unfortunately, the method also encompasses the use of high concentration and hence large volumes of isopropanol to stop the autolysis and precipitate the pancreatin.

Pancreatin can also be produced by removing water from the comminuted pancreas, by freeze-drying, vacuum drying or the like followed by a fat-extraction step with organic solvents such as acetone. alcohols and ether. The use of acetone for defattening is commonly known (Melcer et al., U.S. Pat. No. 3,168,448; Lewis U.S. Pat. No. 3,956,493). Since the defattening step is not performed on the concentrated pancreatine but rather, on cruder preparations thereof, large quantities of solvents are required. WO 91/07948 of Atzl et al., published Jun. 13, 1991, for example, teaches the use of 4000 liters of acetone for 1000 kg of pancreas pulp.

Traditional methods of pancreatin production also teach the use of large volumes of isopropanol: at a concentration of 10% to 20% (v/p) for autolysis, 20% (v/v) for the extraction step and 80% (v/v) for the precipitation. Since large volumes of pancreas preparations are treated, large quantities of solvent, such as isopropanol, are used.

In view of the problems associated with the management of organic solvents and the costs thereof, there thus remains a need for a method of pancreatin production which minimises the use of organic solvents.

There also remains a need for a method of pancreatin production which enables the obtention of a pancreatin containing less traces of organic solvents than conventionally produced pancreatin preparations.

The present invention seeks to meet these and other needs.

The instant description found herein refers to a number of documents, the content of which is herein incorporated by reference.

SUMMARY OF THE INVENTION

It is therefore an aim of the present invention to provide a simple and effective method of preparing pancreatin which minimizes the use of organic solvents.

It is an additional aim of the present invention to provide a simple and effective method of preparing pancreatin on a large scale, wherein the extraction and concentration of the enzymes are performed with minimal amounts of organic solvent.

Further, it is an aim of the instant invention to provide a method wherein a decrease in the viscoi of the pancreas preparation and a significant diminution of the microbial load is operated in a single step.

It is yet another aim of the present invention to provide a method for preparing pancreatin that enables the obtention of a pancreatin preparation which contains less traces of organic solvents than conventional pancreatin preparation methods. In a related matter it is an aim of the present invention to provide a pancreatin preparation which contains less traces of organic solvents than conventionally by prepared pancreatin preparations. It is further an aim of the invention to provide a pancreatin preparation which displays at least equivalent enzymatic activities as conventionally prepared pancreatin preparations.

It is another aim of the present invention to provide a method of preparing a pancreatln concentrate which avoids a precipitation step which can be accompanied by significant losses of enzymatic activity. Further, it is an aim of the present invention to provide a method of producing pancreatin, whereby the defatting of the mixture is effected on an active pancreatin preparation.

In a broad aspect. the present invention provides a method of preparing pancreatin, whereby the defatting of the mixture is effected on an active pancreatin preparation.

More specifically, the present invention provides a method for preparing a pancreatin concentrate having very low amount of residual organic solvent, comprising the steps of:

a) incubating in a fed-batch manner a pancreatic tissue paste with a mixture comprising a viscosity reducing agent and an antimicrobial agent, for 2 to 7 days in order to produce an autolysed and decontaminated pancreatic mixture having a viscosity which enables ultrafiltration thereof, wherein said viscosity reducing agent is present at an initial concentration that is sufficient for reducing the viscosity of the pancreatic tissue paste, and wherein said viscosity reducing agent and said antimicrobial agent are then added to reach a final concentration of both of said viscosity reducing agent and said antimicrobial agent that is sufficient to reduce bacterial cell count, to minimize a precipitation of pancreatic enzymes in said pancreatic mixture and to promote ultrafiltration;

b) an extraction step which comprises diluting the pancreatic tissue paste obtained in step a) with an aqueous extraction solution in order to obtain a pancreatic aqueous slurry;

c) subjecting the pancreatic aqueous slurry produced in step b) to an ultrafiltration in order to obtain a concentrated fat-containing pancreatic preparation;

d) drying the concentrated fat-containing pancreatin preparation obtained in step c); and e) defatting the dried concentrated fat-containing pancreatin preparation obtained in step d) in order to obtain said pancreatin concentrate.

The present invention also provides a method for preparing a pancreatin concentrate having very low amount of residual organic solvent while minimizing use of organic solvent, said method comprising:

a) an autolysing step which comprises preparing a pancreatic mixture comprising a pancreatic tissue paste, a viscosity reducing agent and an antimicrobial agent, and incubating said pancreatic mixture for a time sufficient to yield an autolysed and decontaminated pancreatic mixture having a viscosity which promotes ultrafiltration thereof;

b) an extraction step which comprises incubating the pancreatic mixture obtained in step a) with an aqueous extraction solution preferably comprising an enzymatic stabilizing agent in order to obtain a pancreatic aqueous slurry, and centrifuging said slurry to eliminate tissues and particles, thereby obtaining a pancreatic enzyme solution;

c) a concentration step wherein said pancreatic enzyme solution is subjected to an ultrafiltration using an ultrafiltration membrane having a cut-off of from about 5,000- to about 30,000-Da, whereby a retentate is recovered;

d) a drying step wherein said retentate is dried preferably in the presence of at least one enzyme protecting agent, thereby obtaining a dried concentrated fat-containing pancreatin preparation;

e) a defatting step which comprises incubating the dried concentrated fat-containing pancreatin preparation obtained in step d) with an organic solvent to obtain a solvent phase and a pancreatin concentrate phase and separating the solvent phase from the pancreatin concentrate phase; and f) another drying step wherein said pancreatin concentrate phase is dried to remove residual traces of solvent in order to obtain said pancreatin concentrate.

In a preferred embodiment, the present invention features a pancreatin preparation containing less than about 750 ppm of organic solvent. Preferably, the pancreatin preparation contains less than about 500 ppm and more preferably less than 300 ppm of organic solvent.

The term organic solvent as used herein, should be construed as comprising a mixture of more than one organic solvent.

Herein, the term viscosity reducing agent is meant to cover agents which enable the decrease in the viscocity of a pancreatic mxture through a DNA degradation. While the instant invention is demonstrated by performing the autolysis step with isopropanol, the invention is not so limited. Other viscosity decreasing agent may be used using the same principle taught herein. Non-limiting examples include, acetone and ethanol. Without being limited to a particular model, such agents stabilize the endogenous DNAses present in the pancreatic mixture. it shall be understood that the viscosity reducing agent will be chosen so as to not inhibit autolysis of the pancreatic paste.

Isopropanol is a favoured viscosity decreasing agent since it also acts as an antimicrobial agent. Notwithstanding, isopropanol shares this dual property with other agents. Non-limiting examples of such dual agents include acetone and ethanol. It should be understood that the preferred embodiment described herein provides the advantage of enabling the autolysis, the antimicrobial treatment and the reduction of viscosity to be carried out in a single step. Nevertheless, it will be apparent to the skilled artisan that a separation of these steps could be carried out without departing from the spirit of the invention. The use of exogenous DNAses could prove to be advantageous under certain conditions.

The autolysis step and decontamination step can be performed for a period of from 2 to 7 days, most preferably from 3 to 4 days. The viscosity as defined in centipoise units (mPa.s; CPS) units is preferably from 5 to 8 CPS, most preferably from 5 to 6 CPS. The pancreatin preparation should respect the standards for microbial contamination. Accordingly, following the autolysis step, (or at a later stage, see below), the bacterial cell count as expressed in colony forming units should be below approximately 500 cfu/g, preferably below approximately 200 cfu/g. The temperature of the autolysis step Is preferably between 10° and 25° C., more preferably between 15° and 20° C. Since the decontamination stop using a solvent such as isopropanol needs to be carried out under hydrated conditions, a decontamination of the fat-containing pancreabn powder. following the drying of the retentate. would not be very efficient for large scale processes. However, although less favored, a decontamination of the pancreatin could be performed following the ultrafiltration step rather than at the autolysis step.

The decrease in viscosity is an important element of the present invention as it enables the ultrafiltration step which could not be performed with a conventional pancreas mixture. In addition, by removing excess water form the pancreatic mixture, the ultrafiltration (which also removes salts, proteolytic residues and the like) enables the production of pancreatin having a high enzymatic activity following the drying step.

The preferred drying step, in accordance with the present invention is by spray drying, although non-limiting examples of other drying procedures include air drying. drying with solvents, and freeze drying. Spray drying according to the present invention regularly retains 80% or more of the enzymatic activity intitially present in the pancreas paste (80% or more of the enzymatic activity can be obtained). Performing the spray drying step without the removal of water, operated by the ultrafiltration on the other hand, yields a pancreatin having approximately 30% of its original enzymatic activity.

The instant extraction procedure is also distinguishable from the common extraction methods which utilize a mixture of water and organic solvent (30–70%). In accordance with the instant invention, the extraction Is performed In minimal amounts of organic solvent, preferably 8–10%(v/v).

Preferably, the organic solvent concentration chosen is not sufficient to provoke protein precipitation yet permits a reduction of the viscosity of the mixture to an adequate level of about 5 to 8 CPS.

In order to maintain the stability of the enzyme, enzyme stabilizer are preferably added to the mixture. The instant invention therefore also provides an extraction solution that stabilizes the proteolytic, lipolytic and amylolytic enzymes of the pancreas. Although the preferred embodiment is exemplified with starch, the stabilizing agent does not need to be limited to starch, since other enzyme stabilizing agents are known to the skill artisan to which the present invention pertains. Starch is nevertheless preferred as it protects the amylases which are more susceptible to degradation than lipases and proteases. Non-limiting examples of enzyme stabilizing agent which can be used in accordance with the present invention include sorbitol, glycerol, polyvinyl alcohol, bovine serum albumin, salts, and the like. The preferred embodiment described herein combines starch, sorbitol and salts.

In contradistinction to conventional methods whereby the concentration step is carried out by precipitation (i.e. with organic solvents), the instant invention provides a concentration step by ultrafiltration. As stated above, the role of the viscosity decreasing agent is important to permit an efficient ultrafiltration step. Without a viscosity reducing agent as taught herein for example with isopropanol added in a fed-batch manner, the pancreatic mixture is too viscous to be ultrafiltrated, due to the high undigested DNA content thereof. Preferably the membrane cut-off is between 5,000 and 30,000 Da and more preferably between 10,000 and 20,000 Da. As will be understood by the skilled artisan, the cutoff of the ultrafiltration membranes will be adapted as a function of particular needs of time of filtration, acceptable losses of protein and the like. The number of membranes should be chosen in order to enable the carrying of the ultrafiltration step under conditions which minimize protein denaturation, such as in about 3 hours, and preferably in 1–2 hours.

For the spray-drying step the optimal inlet temperature is around 150°–225° C., and the outlet temperature is around 60°–80° C., preferably the inlet and outlet temperatures are around 175°–200° C., and 65°–75° C., respectively, and more preferably, the inlet and outlet temperatures are around 185° C., and 65° C., respectively. The addition of an enzyme protecting agent such as starch to the retentate, prior to spray drying, is preferable to maintain the activity of the pancreatic enzymes. Another non-limiting example of enzyme protecting agent include arabic gum, maltodextrins, gelatin and sugar.

Defattening agents are well known in the art and although hexane is preferred, other non-limiting examples of defattening agents include ether, acetone, alcohol, trichloroethylene and dichloromethane. Although a defatting step of 30 to 120 min is preferred, it can be increased to overnight without a significant loss in enzyme activity and yield of pancreatin. By defatting a dried concentrated fat-containing pancreatin preparation, the present invention significantly minimizes the use of organic solvents. It shall be understood that a defatting following the ultrafiltration, but prior to the drying of the concentrate could also be performed, as it would still permit, albeit to a lesser extent, a reduction in the use of organic solvents.

A drying step following the defatting can be carried out by conventional methods such as air drying or under vacuum.

Other objects, advantages and features of the present invention will become more apparent upon reading of the following non-restrictive description of preferred embodiments which are exemplary and should not be interpreted as limiting the scope of the present invention.

DESCRIPTION OF THE PREFERRED EMBODIMENT 109 kg of deep frozen hog's pancreas was partially thawed and chopped in a meat chopper. The resultant pancreas paste was mixed with 600 gr. of $CaCl_2$, 300 gr. of NaCl, and 10 liters of isopropanol at the onset of autolysis (t=0 days). At day 2, an additional 15 liters of isopropanol was added (fed-batch procedure). The mixture was then incubated for a further 2 days at 20° C.

The autolyzed and decontaminated pancreatic paste was mixed with 216 liters of water, pH 5.5–7.0, containing 50 mM of NaCl. 0.1% of Starch, and 1% of Sorbitol, The pancreatic slurry was incubated in a 500 L container with gentle agitation for 3 hours, at a temperature of 15°–20° C. The slurry was then centrifuged in order to remove the tissues and the particles to yield a pancreatic enzyme solution. The final concentration of isopropanol as provided by the autolysis step, is approximately 8% (v/v). Such a final concentration of isopropanol is insufficient to provoke protein precipitation and hence a loss of yield.

The supernatant thereby obtained was (380 liters) concentrated by ultrafiltration. Ultafiltration was performed with an Alpha Laval™ ultrafiltration unit, at 30 psi inlet pressure, 20 psi outlet pressure, and at a temperature of 15°–20° C. Six Amicon™ membranes were used for the ultrafiltration (10,000 Da cut-off). The membranes had a surface area of 25 $ft^2$ each, the flow rate of permeate was 4 l/min, the ultrafiltration was completed in 60 min. and 110 liter of the retentate was recovered. Membranes having cut-offs of from 5–30 kDa could also be used in accordance with the present invention. At the lower end (5 kDa), clogging and increased time of filtration is foreseen while at the higher end (30 kDa), a certain loss of protein is expected prior to the formation of the polarization layer.

0.46% of soluble starch was then added to the retentate and spray-dried with a Niro™ spray-drier having a capacity of 60 kg. of water evaporation/hour. Using an Inlet temperature of around 180° C., and an outlet temperature of around 65° C., 22 kg of concentrated pancreatin was obtained.

The concentrated pancreatin was mixed with 1.3–1.5 volume of hexane (25 liters) (60 min, 15°–20° C.) and centrifuged with a basket centrifuge. The pancreatin concentrate was treated with dried air to remove residual traces of hexane. The used hexane can then be recovered by distillation.

The pancreatin thereby prepared showed the following profile:
Pancreatin yield: 16,5 kg
Protease: 250–270 USP/mg
Amylase: 300–320 USP/mg
Lipase: 47–50 USP/mg
Loss on drying: 1,5–3,0%
% fat: 2–4%

EXAMPLE 1

Role of Isopropanol on the Viscosity and Microbial Count of the Pancreas Solution During Autolysis The pancreatic mixture at the concentration stage is very viscous as exemplified in Table 1. Such a high viscosity is not conducive to ultrafiltration. This viscosity can at least in part be explained by the presence of a high content of non-digested DNA in the pancreatic mixture. The addition of isopropanol in fed-batch is shown to significantly reduce the viscosity of the pancreatic solution (Table 1). Without being limited to a particular model, this phenomenon could be explained by the direct DNAse activity which is intrinsic to the pancreas. The fed-batch procedure would permit a stabilization of the DNAse in 10% isopropanol thereby enabling digestion of pancreatic DNA. It would appear that starting at 15% isopropanol the DNAse activity would be less efficient as assessed by the viscosity of the pancreatic solution. The addition of an additional 15% of isopropanol (total of 25%) at day 2 enables the obtention of an adequate viscosity.

TABLE 1

| Isopropanol concentration | day 1 | day 2 Viscosity in CPS | day 3 |
|---|---|---|---|
| 10%* | 6,51 | 5,5 | 5,2 |
| 15%* | 10,2 | 8,9 | 8,0 |
| 20%* | 38,8 | 21,7 | 15,2 |
| 25%** | 6,6 | 5,8 | 5,6 |

*Isopropanol was added at the onset of the autolysis step
**Isopropanol was added in fed-batch: 10% at the onset (day 0) and an additional 15% at day 2.

Moreover the addition of isopropanol permits a significant reduction in microbial counts (Table 2).

TABLE 2

| Isopropanol concentration | day 1 | day 2 CFU/g | day 3 | day 4 |
|---|---|---|---|---|
| 10% | 95000 | 31000 | 28000 | 44000 |
| 15% | 20000 | 13000 | 13000 | 17000 |
| 20% | 1600 | 900 | 720 | 610 |
| 25%** | 80000 | 750 | 400 | 120 |

**In fed-batch as for table 1: 10% the onset (day = 0) and an additional 15% at day 2

The addition of isopropanol in fed-batch hereby permits a DNA digestion in the initial stages of the autolysis step while the increased concentration thereof enables a significant reduction of the microbial load. It will be apparent that addition of exogenous DNAse could under selected conditions be contemplated.

EXAMPLE 2

Comparison of the Organic Solvent Content of Differently Produced Pancreatin Preparations The pancreatin preparation prepared as described above pancreatin 1 and commercially available pancreatin preparations produced by conventional methods (pancreatins a–d) were analysed to compare their contents of residual organic solvents. The nature of the organic solvents used for the production of these commercial pancreatin preparations was determined by gas chromatography-mass sprectroscopy, according to conventional methods. Briefly, the remaining organic volatile impurities were measured using the headspace gas chromatograph method IV of #467 (United States Pharmacopia XXIII, 1995). As shown in Table 3, the pancreatin preparation of the present invention contains a significantly lower amount of residual organic solvent. Such a pancreatin preparation, having about 20 times less residual solvent, as compared to pancreatins prepared acording to conventional methods, provides the advantage of diminishing health hazards associated with organic solvent exposure.

TABLE 3

|  | Solvents | Concentration[1] | RA[2] |
|---|---|---|---|
| Pancreatin 1 | Hexane | 0,31[3] | 1,00 |
| Pancreatin a | Isopropanol | 9,20 | 29,68 |
| Pancreatin b1 | Isopropanol | 4,96 | 16,00 |
| Pancreatin b2 | Isopropanol | 10,50 | 33,87 |
| Pancreatin c | Isopropanol | 7,96 | 25,68 |
| Pancreatin d | Acetone | 2,30 | 7,42 |
|  | Isopropanol | 9,83 | 31,71 |
| Pancreatin e | Acetone | 1,05 | 3,39 |

[1]ppm × $10^3$ (ug/g)
[2]Relative amounts
[3]Average of three experiments

Although the present invention has been described hereinabove by way of preferred embodiments thereof, it can be modified, without departing from the spirit and nature of the subject invention as defined in the appended claims.

What is claimed is:

1. A method for preparing a pancreatin concentrate having very low amount of residual organic solvent, comprising the steps of:

a) incubating in a fed-batch manner a pancreatic tissue paste with a mixture comprising a viscosity reducing agent and an antimicrobial agent, for 2 to 7 days in order to produce an autolysed and decontaminated pancreatic mixture having a viscosity which enables ultrafiltration thereof, wherein said viscosity reducing agent is present at an initial concentration that is sufficient for reducing the viscosity of the pancreatic tissue paste, and wherein said viscosity reducing agent and said antimicrobial agent are then added to reach a final concentration of both of said viscosity reducing agent and said antimicrobial agent that is sufficient to reduce bacterial cell count, to minimize a precipitation of pancreatic enzymes in said pancreatic mixture and to promote ultrafiltration;

b) an extraction step which comprises diluting the pancreatic tissue paste obtained in step a) with an aqueous extraction solution in order to obtain a pancreatic aqueous slurry;

c) subjecting the pancreatic aqueous slurry produced in step b) to an ultrafiltration in order to obtain a concentrated fat-cantaining pancreatic preparation;

d) drying the concentrated fat-containing pancreatin preparation obtained in step c); and e) defatting the dried concentrated fat-containing pancreatin preparation obtained in step d) in order to obtain said pancreatin concentrate.

2. The method of claim 1, wherein the viscosity of said pancreatic aqueous slurry is between approximately 5 to 8 centipoise units.

3. The method of claim 2, wherein the viscosity of said pancreatic aqueous slurry is between approximately 5 to 6 centipoise units.

4. The method of claim 1, wherein a bacterial cell count of said pancreatic mixture following step a) as expressed in colony forming units per gram, is below approximately 500.

5. The method of claim 1, wherein said pancreatin concentrate contains less than about 750 ppm of residual solvent.

6. A method for preparing a pancreatin concentrate containing less than about 750 ppm of residual solvent, comprising the steps of:

a) incubating for 2 to 7 days a pancreatic tissue paste with an agent which acts as both a viscosity reducing agent and an antimicrobial agent, in order to produce an autolysed and decontaminated pancreatic mixture having a viscosity which promotes ultrafiltration thereof; said step a) being conducted in a fed-batch manner wherein said agent is present at an initial concentration which is sufficient to reduce the viscosity of said pancreatic tissue paste, and wherein the concentration of said agent is then increased to reach a final concentration which is sufficient to reduce bacterial cell count, to minimize a precipitation of pancreatic enzymes in said pancreatic mixture and to promote ultrafiltration;

b) an extraction step which comprises diluting the autolysed and decontaminated pancreatic mixture produced in step a) with an aqueous extraction solution in order to obtain a pancreatic aqueous slurry;

c) subjecting the pancreatic aqueous slurry produced in step b) to an ultrafiltration in order to obtain a concentrated fat-containing pancreatic preparation;

d) drying the concentrated fat-containing pancreatin preparation obtained in step c) in presence of at least one enzyme protecting agent; and e) defatting the dried concentrated fat-containing pancreatin preparation obtained in step d) to obtain said pancreatin concentrate.

7. The method of claim 6, wherein said agent is isopropanol and the initial and final concentrations in step a) are about 10% (v/p) and about 25% (v/p), respectively.

8. A method for preparing a pancreatin concentrate having very low amount of residual organic solvent while minimizing use of organic solvent, said method comprising:

a) an autolysing step which comprises preparing a pancreatic mixture comprising a pancreatic tissue paste, a viscosity reducing agent and an antimicrobial agent, and incubating said pancreatic mixture for a time sufficient to yield an autolysed and decontaminated pancreatic mixture having a viscosity which promotes ultrafiltration thereof;

b) an extraction step which comprises incubating the pancreatic mixture obtained in step a) with an aqueous extraction solution to obtain a pancreatic aqueous slurry, and centrifuging said slurry to eliminate tissues and particles, thereby obtaining a pancreatic enzyme solution;

c) a concentration step wherein said pancreatic enzyme solution is subjected to an ultrafiltration using an ultrafiltration membrane having a cut-off of from about 5,000- to about 30,000- Da, whereby a retentate is recovered;

d) a drying step wherein said retentate is dried thereby obtaining a dried concentrated fat-containing pancreatin preparation;

e) a defatting step which comprises incubating the dried concentrated fat-containing pancreatin preparation obtained in step d) with an organic solvent to obtain a solvent phase and a pancreatin concentrate phase and separating the solvent phase from the pancreatin concentrate phase; and f) another drying step wherein said pancreatin concentrate phase is dried to remove residual traces of solvent in order to obtain said pancreatin concentrate.

9. The method of claim 8, wherein the viscosity of said pancreatic enzyme solution is between approximately 5 to 8 centipoise units.

10. The method of claim 8, wherein:

in step a), the pancreatic mixture comprises said pancreatic tissue paste, $CaCl_2$, NaCl and isopropanol acting as both said viscosity reducing agent and antimicrobial agent, said isopropanol being present at an initial concentration of 10% (v/p) in step a), the pancreatic mixture is incubated for 2 days at a temperature of about 15° C., at which time a further 15% (v/p) of isopropanol is added to said pancreatic mixture and incubated for 2 further days;

in step b), the autolysed and decontaminated pancreatic mixture having a viscosity which promotes ultrafiltration thereof is diluted with an aqueous extraction solution comprising NaCl, starch and sorbitol to obtain a slurry having a final concentration of isopropanol of approximately 8% (v/v), and said slurry is incubated at room temperature for approximately 3 hours and centrifuged to eliminate tissues and particles, thereby obtaining the pancreatic enzyme solution;

in step c) the pancreatic enzyme solution is ultrafiltered through ultrafiltration membranes having a cut-off of about 30,000 Da;

in step d) the dried fat-containing pancreatin preparation is defatted with hexane for about 60 min at room temperature; and in step f), the pancreatin concentrate phase recovered from step e) is air dried to remove residual traces of solvent.

11. The method of claim 8, wherein the quantity of organic solvent used in step e) is about 10 times less than for pancreatin preparation methods wherein defatting is effected prior to the concentration step.

12. The method of claim 8, wherein the viscosity of said pancreatic enzyme solution is between approximately 5 to 6 centipoise unit.

13. A method for preparing a pancreatin concentrate containing less than about 750 ppm of residual solvent while minimizing use of organic solvent, comprising:

a) an autolysing step which comprises preparing a pancreatic mixture comprising a pancreatic tissue paste. a viscosity reducing agent and an antimicrobial agent, and incubating said pancreatic mixture for a time sufficient to yield an autolysed and decontaminated pancreatic mixture having a viscosity which promotes ultrafiltration thereof, wherein said viscosity reducing agent and said antimicrobial agent is a same agent and wherein said step a) is conducted in a fed-batch manner, said same agent being present at an initial concentration sufficient to reduce said viscosity of said pancreatic mixture, the concentration of said same agent being then increased to reach a final concentration which is sufficient to reduce bacterial cell count, said final concentration being chosen so as to minimize a precipitation of pancreatic enzymes in said pancreatic mixture;

b) an extraction step which comprises incubating the pancreatic mixture obtained in step a) with an aqueous extraction solution comprising an enzymatic stabilizing agent in order to obtain an aqueous slurry, and centrifugating said slurry to eliminate tissues and particles, thereby obtaining a pancreatic enzyme solution;

c) a concentration step wherein said pancreatic enzyme solution is subjected to an ultrafiltration for using an ultrafiltration membrane having a cut-off of from about 5,000- to about 30,000- Da, whereby a retentate is recovered;

d) a drying step wherein said retentate is dried in the presence of at least one enzyme protecting agent, thereby obtaining a concentrated fat-containing pancreatin preparation;

e) a defatting step which comprises incubating the dried concentrated fat-containing pancreatin preparation obtained in step d) with an organic solvent to obtain a solvent phase and a pancreatin concentrate phase and separating the solvent phase from the pancreatin concentrate phase; and f) another drying step wherein said pancreatin concentrate phase is dried to remove residual traces of solvent in order to obtain said pancreatin concentrate.

14. The method of claim 11, wherein said agent is isopropanol and said initial and final concentrates thereof in step a) are about 10% (v/p) and about 25% (v/p), respectively.

15. The method of claim 14, wherein a bacterial cell count of said pancreatic mixture following step a) as expressed in colony forming units per gram, is below approximately 500.

16. The method of claim 15, wherein before step b), the pancreatic mixture of step a) is diluted with water so that the concentration of isopropanol in said pancreatic mixture for said extraction step is about 8–10% (v/v).

17. The method of claim 13, wherein in step d), said at least one enzyme protecting agent is selected from the group consisting of starch, Arabic gum, maltodextrins, gelatin and sugar.

* * * * *